US008996086B2

(12) United States Patent
Chinnock

(10) Patent No.: US 8,996,086 B2
(45) Date of Patent: Mar. 31, 2015

(54) DIGITAL MAPPING SYSTEM AND METHOD

(75) Inventor: Randal B. Chinnock, Southbridge, MA (US)

(73) Assignee: OptimumTechnologies, Inc., Southbridge, MA (US)

( * ) Notice: Subject to any disclaimer, the term of this patent is extended or adjusted under 35 U.S.C. 154(b) by 273 days.

(21) Appl. No.: 13/235,013

(22) Filed: Sep. 16, 2011

(65) Prior Publication Data

US 2012/0071765 A1 Mar. 22, 2012

Related U.S. Application Data

(60) Provisional application No. 61/383,938, filed on Sep. 17, 2010.

(51) Int. Cl.
  A61B 5/05 (2006.01)
  A61B 5/00 (2006.01)
(52) U.S. Cl.
  CPC .............. *A61B 5/0075* (2013.01); *A61B 5/489* (2013.01)
  USPC ........................................... 600/310
(58) Field of Classification Search
  USPC ......... 600/300, 407, 419, 437, 476–480, 473; 356/27–29, 484; 128/916, 898
  See application file for complete search history.

(56) References Cited

U.S. PATENT DOCUMENTS

| 5,699,797 | A | 12/1997 | Godik |
| 5,873,825 | A * | 2/1999 | Mistretta et al. ............... 600/410 |
| 6,230,046 | B1 * | 5/2001 | Crane et al. .................... 600/476 |
| 6,556,854 | B1 * | 4/2003 | Sato et al. ....................... 600/407 |
| 7,341,557 | B2 | 3/2008 | Cline et al. |
| 7,420,151 | B2 | 9/2008 | Fengler et al. |
| 7,722,534 | B2 | 5/2010 | Cline et al. |
| 2002/0016533 | A1 * | 2/2002 | Marchitto et al. ............. 600/310 |
| 2003/0210810 | A1 * | 11/2003 | Gee et al. ....................... 382/128 |
| 2004/0225222 | A1 | 11/2004 | Zeng et al. |
| 2008/0027317 | A1 * | 1/2008 | Wood et al. .................... 600/427 |
| 2010/0177184 | A1 | 7/2010 | Berryhill et al. |
| 2011/0063427 | A1 | 3/2011 | Fengler et al. |

* cited by examiner

*Primary Examiner* — Elmer Chao
(74) *Attorney, Agent, or Firm* — Brian M. Dingman; Dingman, McInnes & McLane, LLP

(57) ABSTRACT

Embodiments of the innovation relate to method for generating an image of a tissue element. The method includes generating, by a visualization system controller, a highlighting image representation of the tissue element within a tissue region based upon a first image of the tissue element captured when a first light source illuminates the tissue region, receiving, by the visualization system controller, a second image of the tissue element within the tissue region when a second light source illuminates the tissue region, combining, by the visualization system controller, the highlighting image representation of the tissue element to the second image of the tissue element to generate a composite tissue image, and delivering, by the visualization system controller, the composite tissue image to an output device.

5 Claims, 11 Drawing Sheets

DIGITAL MAPPING SYSTEM AND METHOD

CROSS-REFERENCE TO RELATED APPLICATIONS

This patent application claims priority to U.S. Provisional Application No. 61/383,938 filed on Sep. 17, 2010, entitled, "DIGITAL MAPPING SYSTEM AND METHOD," the contents and teachings of which are hereby incorporated by reference in their entirety.

STATEMENT REGARDING FEDERALLY SPONSORED RESEARCH OR DEVELOPMENT

Not applicable

REFERENCE TO COMPACT DISK APPENDIX

Not applicable

BACKGROUND

Embodiments of the present innovation generally relates to the field of medical imaging and more specifically relates to enhanced imaging of subsurface blood vessels or other structures of interest that differentially scatter or reflect specific wavelengths of light as compared to tissues that surround these structures.

Various medical procedures require a physician or technician to discern the location of blood vessels (generally called vasculature herein) embedded in bodily tissues and generally covered with one or more layers of translucent or diffuse tissue (for example, skin). The requirement to "find the vein" can be a positive requirement, as is the case for phlebotomy, or it can be a negative requirement, as when the issue is patient safety. For example, the carotid artery is located immediately adjacent to the pharynx and esophagus. If this artery were inadvertently damaged during a procedure in the throat, the consequences for the patient could be dire.

Furthermore, some of these medical procedures are applied inside various bodily orifices, for example the throat. Often, the physician or technician (referred to herein more generally as the "operator"), must rely on an imaging system to see what he or she is doing in these constricted spaces. While some procedures may be performed with direct view imaging systems (that is, imaging systems that use some form of optical relay elements to present a live image to the operator) there has been a general trend to replace these combinations of lens, mirrors, optical fibers, etc with electronic imaging systems, specifically with miniature video cameras connected to electronic displays. Some electronic imaging systems include optical relay systems in which the operator's eye(s) have been replaced by miniature video cameras. More recently, the original, relatively bulky, black and white video cameras have been replaced by miniaturized, full color and/or higher resolution video cameras, said cameras often located in close proximity to the tissue being examined, thereby eliminating most of the elements in the optical relay systems.

When cutting tissue during surgery of the human body or animals, inadvertent damage to vasculature must be avoided. In open surgery, surgeons have a variety of ways of avoiding vasculature, including palpation, gentle proving with instruments, careful dissection, and direct stereoscopic (human) vision (magnified or unaided) to determine tissue topography and/or pulsatile movement of vasculature. However, many open surgeries have been replaced by minimally invasive surgery (MIS) techniques. MIS techniques include percutaneous procedures of the abdomen (laparoscopy), percutaneous procedures of the thorax (thoracoscopy), natural orifice surgery (NOS, e.g., upper gastrointestinal endoscopic surgery, colonoscopic resections), and natural orifice transluminal endoscopic surgery (NOTES, e.g. trans-gastric appendectomy). In many of these MIS procedures, direct palpation is not possible, probing/dissection with instruments is limited, and 3-D vision is generally not available.

Robotic surgery (RS) is also being adopted for a variety of procedures. The same issues relating to inadvertent damage to vasculature apply to robotic procedures, though 3-D optical imaging is more commonly available in surgical robots.

There is an unmet need for an imaging apparatus and related methods of use that will help surgeons avoid inadvertent damage to vasculature during operative procedures in general and during MIS and RS procedures in particular. The imaging apparatus must be substantially real-time (e.g., having a delay shorter than a typical human's ability to detect) and ideally does not compromise the quality of the surgical visualization. Preferably the apparatus can be integrated into instruments without unduly increasing the size of the instruments or introducing any new hazard to patient or user.

SUMMARY

In one embodiment, the present innovation relates to an electro-optical imaging apparatus and computer-based image processing system (collectively, a visualization system) and a method of using the visualization system to aid the intra-surgical detection and mapping of animal, typically human, vasculature, or other tissue elements of interest. The apparatus includes one or more broad-spectrum or "visible" light sources, one or more narrow-spectrum, typically near-infrared (NIR), light sources, one or more optical image sensors, a control system for time-multiplexing illumination and image capture at visible and IR/NIR wavelengths, an image processing system for enhancing the detection of the tissues of interest in the typically IR/NIR images and creating a digitally enhanced "map" of the tissues, herein called a Highlighting Image Representation (HIR), and a display for presenting the HIR combined with the visible light video stream of the surgical site, typically as a real-time overlay. In other embodiments the apparatus may include one or more relatively narrow-spectrum sources operating with central wavelengths other than in the IR/NIR region. Further, other embodiments may be used to detect and/or map types of tissue other than vasculature and, more generally, the image processing system generates a highlighting image representation of the tissue of interest, which image representation is combined with the visible video stream. For convenience herein, but with no loss of generality, "vascular map", "digital vascular map", highlighting image representation or the acronym "HIR" may be used to mean any of the thus generated image representations used to highlight any tissue elements, vascular or otherwise.

The associated method of using the visualization system includes computer-based user controls that allow the operator, for example, to turn the HIR on and off and/or to adjust visualization system parameters for optimum detection and display of the HIR for a variety of surgical conditions. Said adjustments may affect either or both the apparatus and the image processing system. For convenience, the elements of the method that include control of the operation of the visualization system may be considered herein to be an executive control system whilst the elements of the method that manipulate the digital image(s) may be considered the visualization system controller. However, as will be appreciated by one of skill in the art, the division of software controlled functions into separate parts or modules is somewhat arbitrary and is often useful for software development purposes. Thus, all embodiments of the invention may be considered to include a package of one or more software functions which may, for convenience only, be divided into separately named modules.

In an exemplary embodiment, the visualization system includes a silicon-based array imager (a camera), typically having an imaging device such as a CCD or CMOS sensor, and an illumination module including one or more broad-spectrum (i.e., "white light") source or sources and one or more comparatively narrow-spectrum source or sources, wherein the center of the narrow spectrum is in the near-infrared (NIR) region. The visualization system further includes an image processor (generally embodied in a digital computer) and full-color image display unit. As one of skill in the art will readily understand, the various system components are interconnected with wires, cables, and/or other known interconnection apparatuses and/or methods (for example, WiFi). One of skill in the art will further understand that each element described herein will have ancillary elements, perhaps not described herein, that are well known to be necessary for the element's proper function. For example, the camera may include a supporting electronic board that includes power conditioning, digitization, camera control signal generation, input/output, etc. functions and includes an imaging lens for forming an image of the surgical site on the sensor.

In an exemplary embodiment of the visualization system the camera operates at 30 frames per second. During twenty-nine of the thirty frames the target tissue is illuminated with the broad-spectrum source and the camera (and associated conventional camera signal processing) produces a conventional full-color image. During the thirtieth frame the broad-spectrum source is turned off and the narrow-spectrum source (typically NIR) is turned on, whereby the camera produces a substantially monochrome image. It is generally known in the art that vasculature veiled by other bodily tissue are more easily discerned by a silicon-based sensor under NIR illumination; that is, there is relatively higher contrast between vascularized areas and non-vascularized areas with NIR illumination as compared to broad-spectrum ("white light") illumination.

In some exemplary embodiments the illumination module includes multiple light emitting diodes (LEDs). In one embodiment the LED illumination is integrated into the tip of an endoscope along with the camera. This illumination module is able to fit multiple LEDs into the tip of the endoscope. Some of these LEDS are white LEDs, and at least one operates in the NIR. There are separate drive circuits for the NIR and white LEDS to allow them to be turned on and off independently.

In one exemplary embodiment the camera operates at 30 frames per second. In one exemplary operating mode, for 29 of the 30 video frames each second the white LEDs are turned on by the control circuit and the NIR LEDs are off. This illumination timing produces an apparently normal video stream, albeit with a very slight "blink" once per second. During these 29 video frames the camera and visualization system is said herein to be operating in the color imaging mode.

In this particular exemplary operating mode, for the remaining 1 out of the 30 video frames each second, and synchronized with the camera readout clock, the white LEDs are turned off and the NIR LEDs turned on. This creates a single "freeze frame" image of the vasculature, once per second. The system is said to be operating in the NIR mode.

It should be noted that the camera operation is unchanged between color imaging mode and NIR mode. Without further processing, the camera output, if displayed on a monitor, would appear as a normal color video stream of the surface tissue with a once-per-second flash of a reddish tinted image that lacked the details of the surface tissue. However, exemplary embodiments of the visualization system do include further processing.

In exemplary embodiments the image processing system is a digital processor which typically includes custom, semi-custom, or Commercial Off The Shelf (COTS) software, or some combination thereof. Said software may perform one or more unique functions in addition to the typical digital imaging functions for converting camera output signals into the proper drive signals for the selected image display. In one instance, the visualization system controller directs the image processing software to separate the color imaging mode frames from the NIR mode frames. The color imaging mode frames are handled as normal video frames and are sent unmodified to the image display while the NIR mode frames are subjected to additional image processing before being sent to the image display. It will be understood by one of ordinary skill in the digital imaging art that the color imaging mode image frames and the NIR mode frames will be combined into a single image stream where, in one embodiment, the NIR mode frames fill in the gaps in the color imaging mode image stream created when they, the NIR frames, were separated from the input image stream for additional processing. In other embodiments the NIR mode frames may be converted to an image overlay, in which embodiment the overlay is merged with each color mode frame and the one-frame gaps in the image stream would be smoothed over by, for example, repeating one of the immediately temporally adjacent color mode frames.

In a second instance, an exemplary embodiment the image processing software uses a variety of techniques to locate the locus of image points in each NIR mode frame that form the boundaries of the tissue of interest, generally obscured vasculature. The thus processed frame is called a Digital Vasculature Map, indicating that it shows the locations of the vasculature.

For example, one possible process for developing the HIR from the monochromatic image frame includes the steps of:
A) developing a histogram of pixel intensities,
B) triaging the pixels into definitely dark, definitely bright, and transitional
C) in the transitional regions, applying a local operator to determine the state of each pixel (dark or bright),
D) applying a second local operator to connect all dark regions (the veins),
E) applying a third local operator that records the pixel addresses of all edge pixels (viz. pixels at the boundary between bright and dark regions), and
F) creating an overlay image composed of the identified edge pixels.

In a third instance, in an exemplary embodiment of the imager, the image processing software merges the thus generated, most current, HIR with each subsequent color mode frame. Optionally the image processing software can incorporate other ancillary information into the HIR overlay (or as a separate overlay) wherein this additional information would be located in regions of the image in which no vasculature was found (i.e., away from the active pixels in the digital map).

In some embodiments the image processor also includes an executive control system (ECS). The ECS is the interface between an operator and the visualization system apparatus and processing system. For example, the ECS synchronizes the visible and NIR LEDs with the camera frame timing and translates the operator's operational and processing desires into system-appropriate parameter values.

In most exemplary embodiments the visualization system also includes a color display unit. Typically the display is a LCD computer monitor adapted for use in the sterile environment of the surgical theater.

The above and other features of the invention including various novel details of construction and combinations of parts, and other advantages, will now be more particularly described with reference to the accompanying drawings. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE SEVERAL VIEWS OF THE DRAWING

The foregoing and other objects, features and advantages of the invention will become apparent from the following description in conjunction with the accompanying drawings, in which reference characters refer to the same parts throughout the different views. The drawings are not necessarily to scale; emphasis has instead been placed upon illustrating the principles of the invention. Of the drawings.

DETAILED DESCRIPTION OF THE INVENTION

Figure 1A:
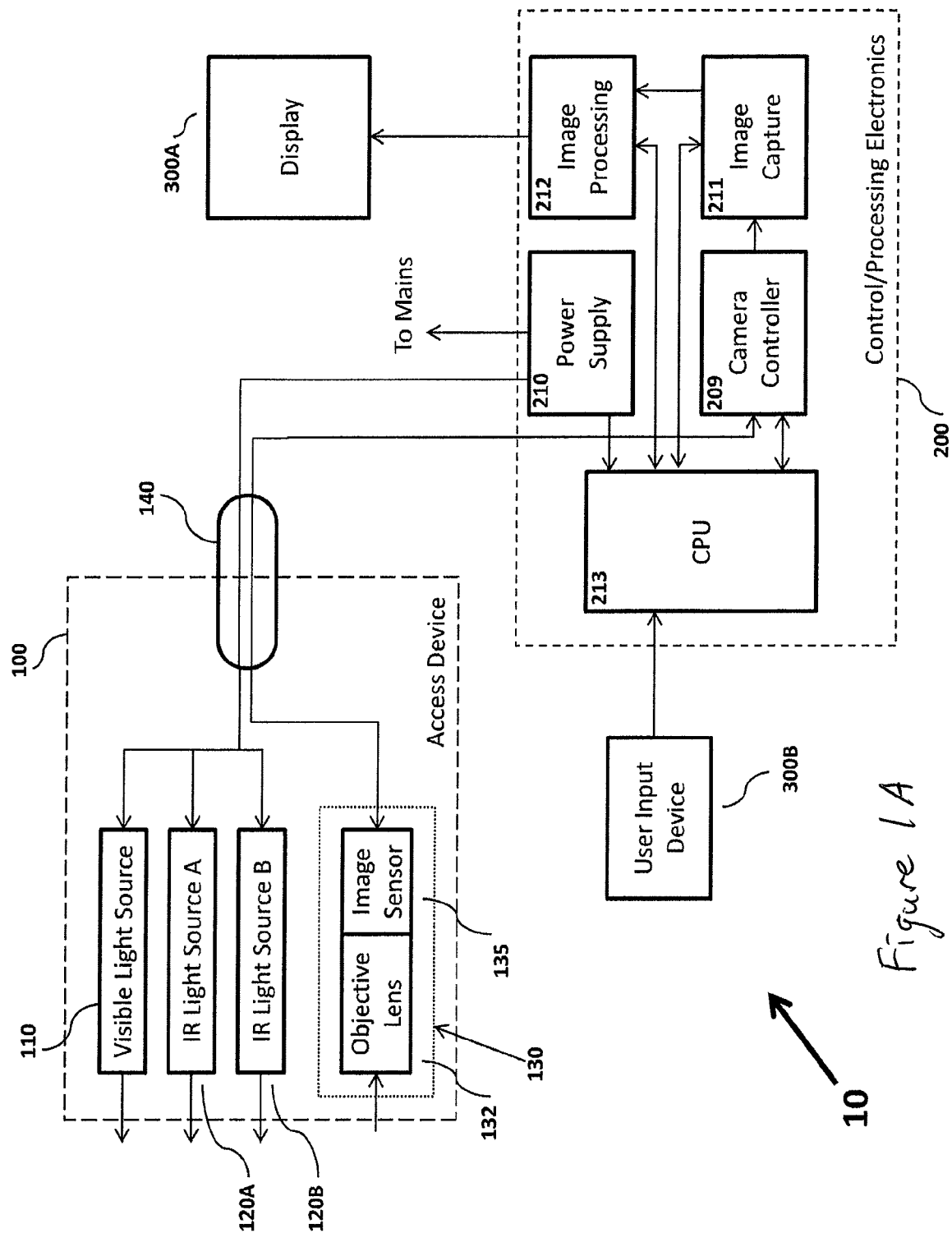
FIG. 1A is a block diagram of the system opto-electronics.
Figure 1B:
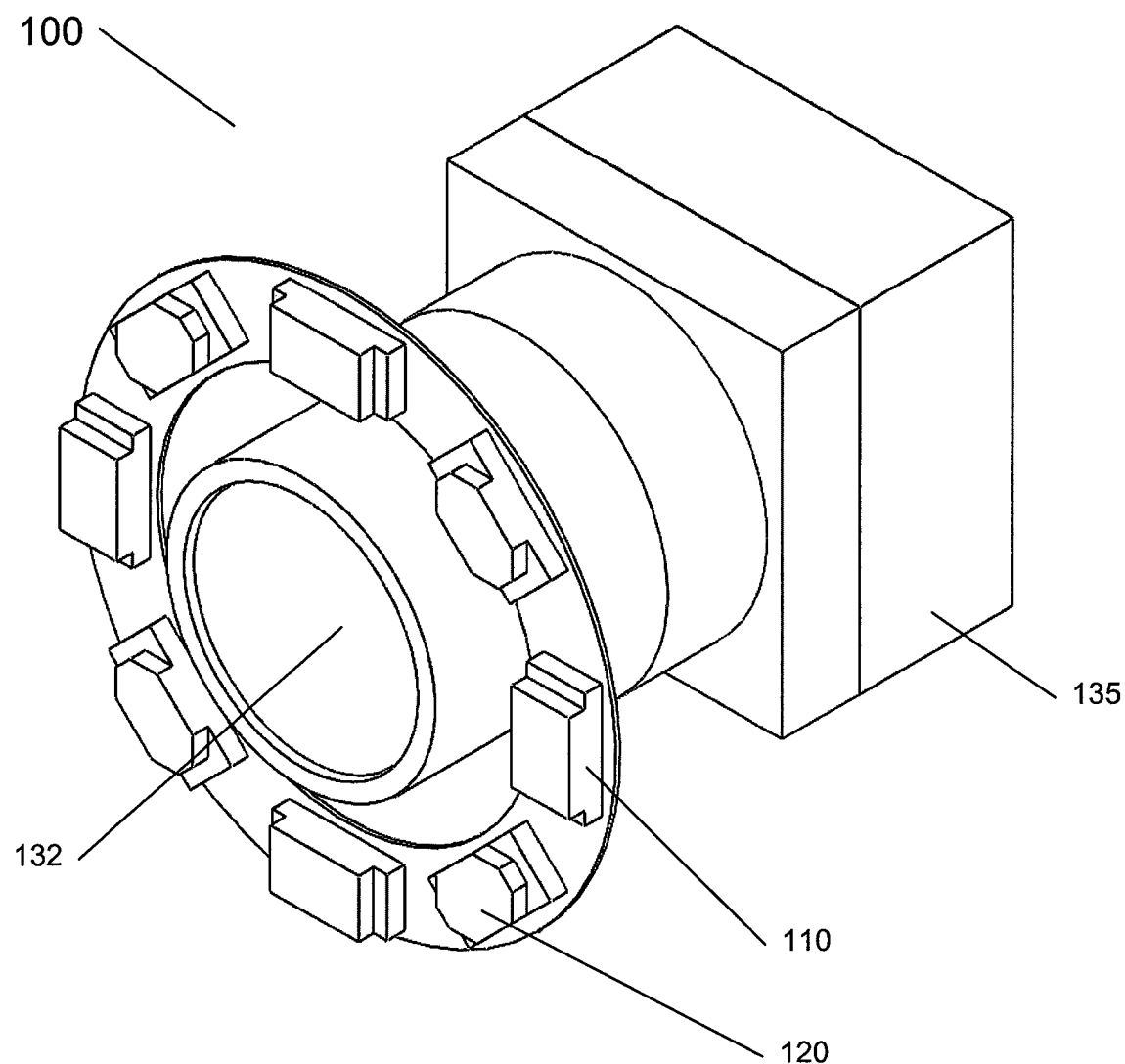
FIG. 1B is a schematic perspective view of an embodiment of the access device

A typical embodiment of a digital mapping (or visualization) system 10 is illustrated in the functional block diagram of FIG. 1A and in the perspective schematic of FIG. 1B. Visualization system 10 includes an access device 100, a computer processing system 200 and an operator interface 300. Access device 100 is used to collect images of a tissue region of interest. One subset of images is acquired with visible wavelength illumination while a second subset of images is collected using narrowband illumination, typically in the near infrared. Computer processing system 200 generates one or more highlighting image representations (HIR) from the narrowband image subset, which representations highlight tissue elements of particular importance to the operator. These HIRs are combined with the visible wavelength image subsets so as to highlight the tissues elements of particular importance within the visible images of the tissue region.

Apparatus

Access device 100 provides physical access to the imaging target region, typically a region of tissue located at a surgical site interior to an animal body. Device 100 may be, for example, a catheter, flexible endoscope, rigid endoscope, snake robot, articulating arm robot, a delivery platform for NOTES procedures such as those available from the company TransEnterix, or other type of device containing one or more lumens for the introduction of instruments inside the body. Processing system 200 typically includes a personal computer system on which various software modules may be run, said modules typically providing operator interface, system executive control, visualization system control, image processing and image display functions. Additionally, processing system 200 may include special electronic circuits and systems, housed in stand-alone enclosures or designed to fit in the computer's enclosure, wherein such circuits and systems perform functions not well suited to the selected computer. Operator interface 300 includes one or more user input devices, such as a keyboard and mouse, and one or more display devices, such as a computer monitor.

Access device 100, in some exemplary embodiments, includes a broadband (also called "visible" herein) light source module 110, a narrowband, or infrared/near infrared, light source module 120, an imaging camera 130, itself having an objective lens 132 an array image sensor 135, as well as miscellaneous supporting optics and electronics understood as needed to make an operational camera. Generally access device 100 further includes an electronic/fiber optic cable 140 to convey data and electrical power between access device 100 and processing system 200.

Visible light source module 110 is typically disposed at the distal tip 101 of access device 100 and includes in one exemplary embodiment one or more white light emitting diodes 112 (LED). The individual sources 112, e.g., LEDs, are disposed to illuminate a region of tissue in front of distal tip 101 with, preferably, substantially uniform illumination. In other embodiments, visible light source module 110 may have one or more groups of monochromatic emitters such as LEDs (e.g., red, green and blue), or one or more lasers, wherein the combined red, green, and blue illumination is functionally equivalent to that from a "white" light source. Visible light source module 110 may, alternatively, have remotely located LEDs, lamps, or lasers whose light is conducted to distal tip 101 via one or more optical fibers incorporated into cable 140. The emitting ends of said optical fibers are, typically, disposed to illuminate a region of tissue in front of distal tip 101 with, preferably, substantially uniform illumination. In some embodiments that include a group of monochromatic emitters, each LED or laser may be configured to be excited or controlled independently.

Narrowband light source module 120, in some embodiments, include one or more infrared or near infrared LEDs or lasers 122, typically located either at the distal tip of access device 100 or disposed remotely with light conducted to distal tip 101 via one or more optical fibers incorporated into cable 140. In some embodiments narrowband light source module 120 includes two source submodules 120A and 120B. The individual sources, e.g., LEDs, are preferably disposed to illuminate a region of tissue in front of distal tip 101 with substantially uniform illumination. All sources are configured to substantially illuminate the same region of tissue. It may be noted that narrowband and visible light source modules/submodules are logical groupings of the one or more physical sources. Hence, as illustrated in FIG. 1B, narrowband LEDs 122 are physically distributed along an annular circuit board 126, being interspersed with visible LEDs 112, even though they are considered to constitute a single narrowband light source module 120.

The wavelengths of submodules 120A, 120B are selected to correspond to the scattering and absorption properties of the tissues being imaged or mapped, the response curve(s) of the detector(s) being used to image the tissues, and/or, in some embodiments, the scattering and absorption properties of oxyhemoglobin and deoxyhemoglobin. In one embodiment, narrowband light source module 120 provides light for example, in the general wavelength range of between 650 to 1000 nm, which illumination wavelength range is generally known to maximize the contrast between vasculature and the surrounding tissues when imaged with a silicon detector. Further, because venous blood contains more deoxyhemoglobin than oxyhemoglobin, and arterial blood contains more oxyhemoglobin, the spectral imaging characteristics of veins are different from the spectral imaging characteristics of arteries. It is, therefore, advantageous in some embodiments to select different wavelengths for each of the narrowband light source submodules 120A and 120B. In one embodiment for example, narrowband illumination centered at wavelengths of 700 and 1000 nm, which has been shown to be useful for differentiating veins from arteries, is selected for submodules 120A and 120B respectively. The submodules are independently time-multiplexed with visible light source module 110 to create two separate overlay images; one highlighting the veins, one highlighting the arteries. In yet other embodiments it may be advantageous to have more than two narrowband light source submodules, with the additional sources having substantially unique wavelengths and independently controllable drive circuits.

In one exemplary embodiment, visible illumination module 110 includes white light LEDs, part number APT1608QWF/G, available from Kingbright Corp., 225 Brea Canyon Road City of Industry, Calif. 91789. Each LED typically transmits a luminous intensity of 450 mcd of broadband illumination when operating in accordance with at manufacturer's recommendations. In the exemplary embodiment, narrowband light source module 120 is configured as NIR light LEDs, part number APT1608SF4C-PRV, also available from Kingbright Corp, Each IRLED is capable of transmitting 1.5 mW/sr of luminous intensity at a narrow band centered at 880 nanometers.

Returning to FIG. 1A, objective lens 132 forms an image on image sensor 135 of a tissue region surrounding the target tissue, having been directed to that region by the operator. Preferably objective lens 132 is designed for low chromatic aberrations throughout the full range of visible and IR wavelengths selected for the particular embodiment. Such a design, e.g., low chromatic aberration, is used to co-register the images formed by the different wavelengths, preferably to pixel level accuracy. The lens elements may be glass, injection molded plastic, diffractive, or a combination thereof and, preferably, has a broad band anti-reflection coating designed for the full wavelength range of the embodiment.

Camera 135 in visualization system 10 preferably produces color images that render the colors of the tissue region on display 300A with sufficient accuracy that the operator is not mislead, for example, in his or her judgment of the condition of the tissue region. Such color accuracy, if not achieve inherently from the selection of the visible illumination module's LEDs, is readily achieved through well know calibration procedures and digital imaging techniques. For example, many still and video digital cameras have an "automatic white balance" feature built in. Alternatively, many photographers use a gray card or specially designed color reproduction calibration cards and software to correct their camera/processing "white balance". See, for example, the ColorChecker Passport from X-Rite, Inc., 4300 44th St. SE, Grand Rapids Mich. 49512.

Additionally, camera 130 preferably has sufficient resolution to allow the operator to perform fine-scale, critical surgical tasks and is small enough to fit into access device 100. Image sensor 135 is typically a 2-D silicon detector array. When the system is configured with a visible light source, image sensor 135 typically has a color matrix filter such as a red, green, and blue Bayer array mounted immediately in front of the detector array to produce full color images from each frame. Such detectors are generally available as commercial-off-the-shelf (COTS) items. Bayer type filter arrays are typically transmissive in the near-IR wavelengths, allowing the same image sensor to be used for imaging in both the visible and the near-IR (viz., with wavelengths out to approximately 1000 nm). In one exemplary embodiment, detector array 135 is a 400×400 HVGA array, PN OV06930 from OmniVision Technologies, Inc., 4275 Burton Drive, Santa Clara, Calif. 95054

In another embodiment no Bayer type filter is installed, in which case full color imaging is still possible if the visible light source module provides a sequence of monochromatic (nominally red, green, and blue) light pulses in synchrony with the image frames on the (broadband) monochrome detector array. In this embodiment, processing electronics 200 temporarily stores and then digitally combines each series of frames to create a composite color image. This mode of operation is known as field sequential imaging.

In another embodiment of field sequential imaging, visible light source module 110 and narrowband light source submodules 120A,B are embodied as series of monochromatic sources having output throughout the visible and NIR ranges of wavelengths. In this embodiment all of the individual monochromatic sources are pulsed sequentially and in synchrony with a series of frames on a single monochrome detector array. The frames collected while the visible light source module LEDs are illuminated are used to construct natural color images and the frames during the NIR illumination are used to construct the HIR. It should be noted that the sequence in which the various light sources are pulsed in field sequential imaging is determined as a design choice based on the properties of the individual sources (e.g., LED intensity), detector properties (e.g., wavelength dependent sensitivity), or system needs (e.g., duty cycle of NIR versus visible image frames).

As will be understood by one of skill in the art, there are many alternative configurations for image sensor 135 that provide an equivalent capability for capturing visible and IR images. For example, a sensor with a unique matrix filter with elements optimized to transmit combinations of both visible and one or more IR wavelengths may be used. Another alternative is to fabricate camera 130 with two image sensors and a beamsplitter. Said beamsplitter is optimized to direct visible wavelengths to an image sensor optimized for visible detection while simultaneously directing NIR wavelengths to an image sensor optimized for NIR detection. A further alternative is to use a more complex beamsplitter block to divide the image into n spectral bands, and n detectors, each optimized for one spectral band. The images from each of the n detectors are then digitally combined to form one visible image and one NIR image. The use of multiple detectors results in the highest image resolution for a given pixel count of any one sensor.

Cable 140 electrically connects the components located at the distal end of the instrument to, typically, an enclosure (not illustrated) containing control/processing electronics 200. Cable 140 may carry clock pulses and control signals from a camera controller 209 in enclosure to image sensor 135. Additionally, cable 140 may carry power from the enclosure to image sensor 135 and light source modules 110 and 120. Further, cable 140 may carry the output signals from image sensor 135 to the enclosure in analog or digital form. Cable 140 may alternatively be divided into more than one cable or includes both electrical and fiber optic elements.

The enclosure typically contains one or more power supplies 210 to provide power for the entire digital mapping system 10 including, in some embodiments, the visualization system controller 213, camera controller 209, specialized circuit electronics (e.g., image capture circuit 211 and image processing/display adaptor 212), and the one or more light source modules in access device 100. The enclosure also, in some embodiments, hosts operator interface 300

Operator interface 300 has one or more typical computer human interface devices, e.g., keyboard, mouse, or trackball, illustrated in FIG. 1A as element 300B, and a video capable display 300A. Display 300A may be any of several known kinds of displays with adequate color accuracy, resolution, and refresh rate as required by the system designer. A resolution of at least 640×480 pixels and a refresh rate of at least 60 Hz are typically required. In one preferred embodiment display 300A is a 19" widescreen TFT LCD monitor with 1440×900 resolution.

Conventionally, camera controller 209 provides appropriately conditioned power, clock pulses, and setup commands to image sensor 135. In one system architecture, an image capture circuit 211 captures the video output from the image sensor. This circuit may include buffering and signal conditioning functions that prepare the signal for digital processing and/or display. All signals are transferred from image capture circuit 211 to image processing/display adaptor 212. Visualization system controller 213 instructs adaptor 212 what, if any image processing is to be performed on the various images in the data stream. In some embodiments, adaptor 212 may include image buffers for temporarily storing image frames. In some embodiments visualization system controller 213 includes memory for long term image storage. Such long term storage is typically embodied as hard disk drives. Long term storage provides an archive of the video that the operator saw during, say, a surgical procedure.

In another system architecture, all image processing is performed within visualization system controller 213, in which architecture image processing/display adaptor 212 is generally replaced functionally by a conventional computer display adaptor.

In some embodiments user interface 300 is substantially identical to the interfaces used with personal computers. In these embodiments, an operator runs the visualization system using menus, typed commands, soft switches, etc., as are typically used in commercially available software packages. In other embodiments, user input device 300B may be configured as a touch screen, membrane panel, one or more individual hardware switches and/or potentiometers, joystick, voice command circuit, foot control, or a combination thereof, in which embodiments the enclosure may be adapted to include a unique control panel, designed to accommodate the selected user interface elements.

As has been noted above, in some embodiments the enclosure, visualization system controller and user interface may include a customized personal computer into which one or more specialized "cards" have been installed. These "cards" are printed circuit boards which have been designed to conform to the applicable PC bus standards. The PC bus is interface through which the card and the computer communicate data and power. In some visualization system 10 embodiments, a PC based enclosure may have a combination of commercially available cards and custom fabricated cards. An example of the former is the Cognex MVS-8500 Machine Vision, PCI-Express bus Frame Grabber, available from Cognex Corporation, One Vision Drive, Natick, Mass. 01760. Alternatively, some PC-based embodiments of the vision system may use "stand alone" elements. For example, Cognex Corporation also provides FireWire digital cameras that connect directly to PCs without requiring a frame grabber. The FireWire high-speed digital interface uses a serial bus to transmit monochrome or color images with resolutions from 640×480 up to multi-megapixel. Cognex supports both the IEEE 1394a FireWire standard and the high speed IEEE 1394b FireWire B cameras. The apparatus described above collects one or more images of a tissue region, the images being a combination of visible light images and narrowband light images. Visualization system controller 213 and/or image processor/display adaptor 212 receives these images and applies one or more digital imaging processing techniques to generate a Highlighting Image Representation (HIR) from the narrowband light images, which representation is then combined with one or more of the visible light images before being sent to display 300A.

Figure 2:
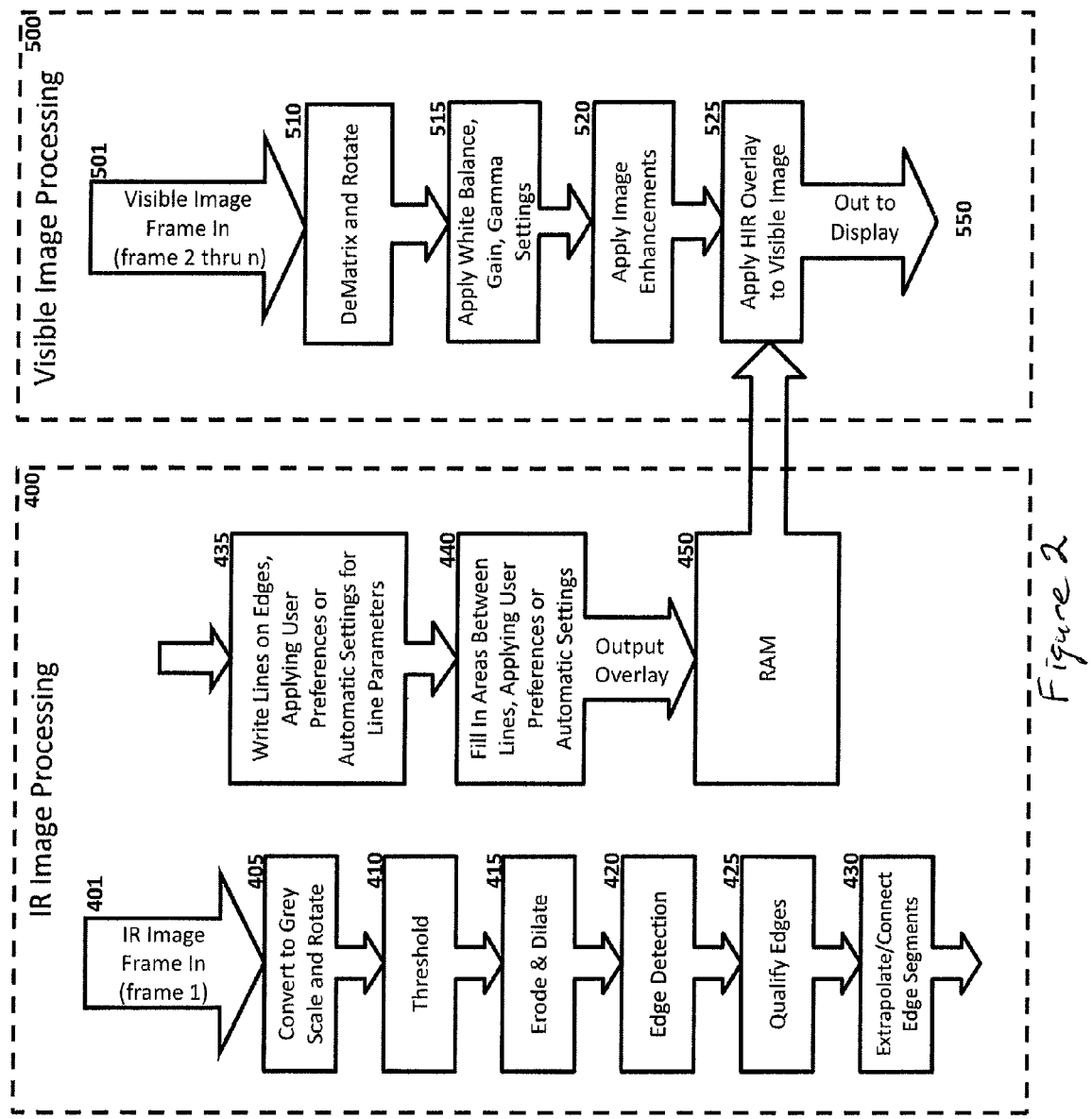
FIG. 2 is a functional flow diagram of an exemplary image processing procedure set.

FIG. 2 illustrates a functional flow diagram for one exemplary embodiment of a set of an image processing procedures. These procedures can be implemented using any of several open source library of programming functions for real time computer vision, e.g., from OpenCV (Open Source Computer Vision), which is a library of programming functions for real time computer vision available at http://opencv.willowgarage.com/wiki/. In FIG. 2, the functional flow is divided into two sections: a narrowband image processing section 400 (near-IR in this exemplary embodiment), which generates the HIR, and a visible image processing section 500, which generates the HIR. Referring to the figure, NIR image processing starts when a raw narrowband image frame (viz., a frame as recorded by camera 130 when narrowband illumination source module 120 is active and visible illumination source module 110 is deactivated) is transferred from camera 130 at step 401. For convenience this IR image will be referred to without loss of generality as "frame 1". In general, system 10 operates at normal video frame rates (e.g., 30 frames/second) to create an easy to view display for the operator. In one exemplary embodiment NIR frame 1 is followed by a series of n−1 visible image frames. The value of n, the total number of frames in a set, is programmable and determines the HIR rate. For a system operating at the typical video frame rate of 30 frames per second (fps), if n=30 the HIR would be updated once per second. If n=60, the digital map would be updated once every 2 seconds, and so on.

Depending on operator preferences, lighting, or other factors, it is sometimes desirable to take more than one narrowband image in a row. For example, in low illumination situations a single frame may be electronically noisy so it may be desirable to acquire two narrowband frames sequentially, followed by the desired number of visible frames. In general the sequencing of these frames can be expressed as a ratio, say M:N, where M is the number of narrowband images, N is the total number of frames in the set, so that N-M is the number of visible frames that follow the M narrowband frames.

In some embodiments the image sensor includes a matrix filter, such as a Bayer filter; as shown in the exemplary flow diagram, frame 1 is converted to grey scale, step 405 using commonly known methods. If desired, the angular orientation of the image may be rotated during grey scale conversion 405 by re-mapping pixels to alternate locations according to a lookup table (LUT) or mathematical algorithm with the input of information about the rotation magnitude and direction. Alternatively, image rotation may be performed at other points during image processing or display.

Frame 1, in this example, is then "thresholded" at step 415. In some embodiments, thresholding step 410 includes both treating very low luminance valued pixels and very high valued (e.g., saturated) pixels. Pixels that have luminance values below a certain programmable value, particularly if they are embedded in other low-valued pixels, are generally assumed to be noise pixels; these pixels are, typically, set to zero during thresholding operations. Thresholding may also be used to eliminate pixels that have luminance values above a certain programmable value (e.g., saturated pixels). Since saturated pixels have lost their true luminance values, later procedures that involve numerical operations will be degraded by a false, saturated pixel value. In such cases it may be advantageous to mark the pixel(s) as unusable. In other later procedures, such as image display, it may be appropriate, for example, to set the saturated pixels to the average value of their nearest neighbors. In either case, thresholding step 410 is used to improve processing success.

In the exemplary system embodiment it is known, a priori, that the features of the vasculature are fairly large, e.g., they span many pixels. Features that span only a smaller number of pixels are probably spurious and can slow or confound the image processing algorithm. It is therefore desirable, in some embodiments, to eliminate image features below a pre-determined size. As indicated at step 415, commonly known operators such as blob erode and dilate are used in this embodiment to eliminate spurious features in the frame. Erode and dilate coefficients are programmable so that the maximum size of features to be eliminated can be adjusted.

Having removed probable image artifacts from the frame, the next step in this exemplary processing flow is edge detection, step 420. Commonly known edge detection operators are used to determine the likely boundaries of the tissue feature of interest, e.g., vasculature. These operators are based on changes in luminance at the edges of features, i.e., when there is a pre-determined contrast between nearby pixels (that is, the recorded luminance value changes by a programmable number of bits over a programmable number of pixels in a monotonic or quasi-monotonic way), a potential boundary (or edge) pixel is identified as detected at a programmable threshold along the intensity curve.

Typically, edge detection operators also calculate and record the apparent direction of the boundary to which the potential boundary pixel belongs. That is, if the identified contrast is between "east-west" pixels, then the apparent boundary must be running, generally, "north-south". Typical edge detection operators convert potential boundary pixels into actual edge (or boundary) pixels when groups of potential boundary pixels abut (or nearly abut) along the previously identified apparent boundary direction. The thus identified boundary pixels are used to generate boundary segments, the segments being limited in length by how many abutting boundary pixels were detected. Since, in some cases, these boundary segments may be the result of coincidental noise artifacts, edge qualification, step 425, is used to qualify boundary segments based on factors that may include length, number of qualified edge points, morphology, contrast, and proximity to other edges.

The qualified edge or boundary segments are "tied together" by extrapolation (e.g., extending them to connect with adjacent segments), step 430, to define as much of the vasculature as possible. To ensure that segments of contiguous edges are correctly joined, this operation further applies qualifiers such as distance from one segment to the next, segment vector alignment, and segment offsets.

Detected, qualified edges form the basis for a highlighting image representation (HIR) of the vasculature. A common HIR is created by digitally "tracing" over the qualified edges to form constant luminance, monochromatic lines that distinctly outline the underlying vasculature. This "tracing" operation is applied at step 435 of the exemplary embodiment. Generally, the background image information surrounding the traced lines is eliminated from the frame, leaving just the network of lines. The traced lines, when overlaid on, say, a visible-light image, are easily interpreted by a human observer as mapping the locations of the hidden vasculature. Characteristics of the lines, such as their colors, widths, types (e.g. solid or dashed), and opacities can have default values or can be adjusted by the operator. They may also be adjusted dynamically by an automated algorithm to optimize their visibility when overlaid onto backgrounds of different colors and complexities.

If desired, visibility of the HIR when viewed on a display may be enhanced by filling in the spaces between the lines, as indicated in step 440. This fill can be a solid color or a pattern of one or more colors, and may have adjustable opacity, pattern pitch, etc. These parameters may again have default values, be adjusted by the user, or be adjusted dynamically by the algorithm to optimize visibility of the fill against the background on which it is overlaid. The completed digital map of the vasculature is then stored in memory in media such as random access memory (RAM), step 450.

Returning to FIG. 2, visible image processing section 500 starts when at least one raw visible image frame (viz., a frame as recorded by camera 130 when narrowband illumination source module 120 is deactivated and visible illumination source module 110 is activated) is transferred from camera 130 at step 501. As has been described above, many system embodiments operate with an M:N narrowband ratio. In general, then, N-M frames are transferred at input step 501. Also, as was the case with the narrowband image processing section 400, the raw image frame may require "de-matrixing" (conversion from multiple monochromatic camera pixels to full color image pixels) and image rotation, indicated as step 510.

In steps 515 and 520, any image collection settings (such as white balance, global gain, and gamma) that have been stored in memory are applied to the frame and other commonly known image enhancements may be applied, including local gain values, shading corrections, faulty pixel corrections, sub-pixel processing, and edge enhancements. These settings and enhancements all contribute to the final luminance and chrominance values for each pixel, and ensure that maximum resolution is obtained and that actual colors are accurately rendered.

Finally, at step 525, the HIR is retrieved from memory, combined with the processed visible image stream and output 550 to a display. In some embodiments, this combining function is overlaying. That is, on a pixel by pixel basis, the non-zero values in the HIR are substituted for the pixel values in the active frame. The HIR obtained from NIR frame 1 is overlaid onto visible frames 2 through N, after which the whole N frame sequence is repeated, e.g., a new HIR is generated from a new NIR frame 1 and overlaid onto visible frames 2 through N.

Figure 3A:
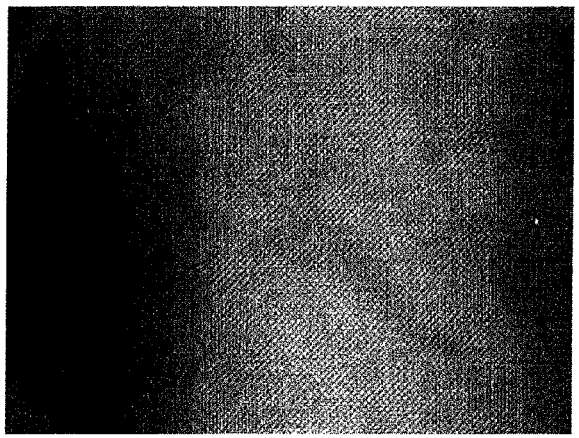
FIG. 3A is an example image of human wrist.
Figure 3B:
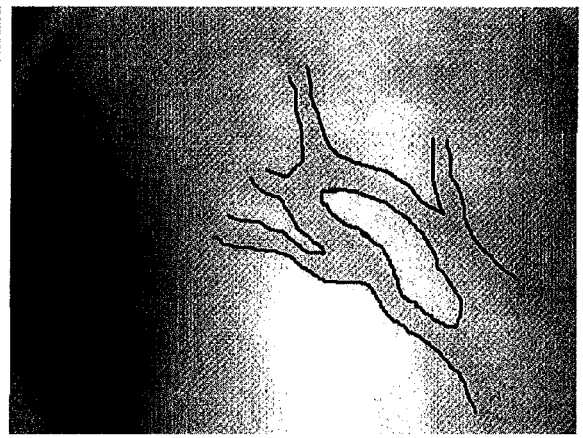
FIG. 3B is a simulation of an HIR overlaid on the image of FIG. 3A.

FIG. 3 illustrates the effect of the exemplary image processing procedures described above. FIG. 3A is an actual digital image of a human wrist, captured under NIR illumination. Had the same wrist been illuminated under visible illumination the vasculature, i.e., the darker gray regions, would have had even less visible since the full color image would be mostly "skin" color. FIG. 3B is a simulation of the vascular HIR that would be generated by a typical visualization system, overlaid on a continuous tone image.

It should be noted that, in many embodiments, the image processing procedures built into visualization system 10 include a number of settings that can be empirically optimized for best system performance under particular imaging conditions. These settings may include, for example, threshold values, erode and dilate widths, edge slopes, edge lengths, edge alignments, and so on. In additional to the user input already described, the user may also have other system inputs, including the ability to turn the HIR on and off, setting the HIR of the vasculature to appear intermittently at a user-settable interval and duration, showing the HIR of the vasculature adjacent to the visible image on the display rather than overlaid, showing the HIR of the vasculature in a picture-in-picture mode on the display, or combinations thereof.

Operation

Figure 4:
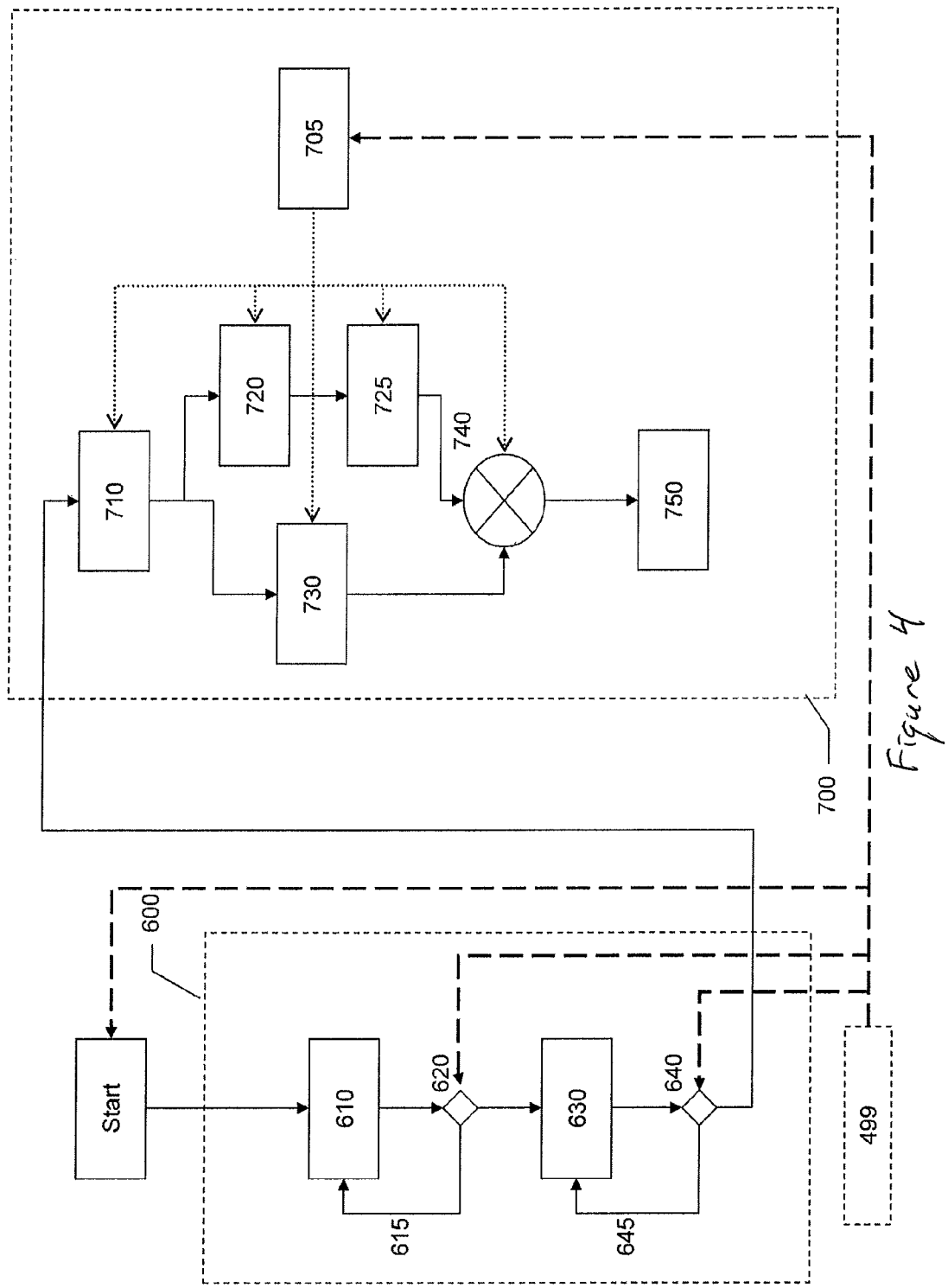
FIG. 4 is an exemplary operational flow diagram for the visualization system.

FIG. 4 is an exemplary top level operational flow diagram for the visualization system as it might be used to assist a vascular surgeon. As indicated, when the system is first started on command by the operator 499 there would be, typically, a Setup phase 600 followed by an Operational phase 700. Typically, Setup phase 600 begins with the system operating as a conventional video imaging system, continuously collecting and displaying visible light images, operation 610. During this time the operator generally adjusts the image collection parameters—illumination level, for example—to his or her liking while viewing the live images on display 300A. Also during this part of Setup 600, the operator will position access device 100 to point at the tissue region of interest. In some embodiments access device 100 is positioned using a robotic device.

Visible image collection and display 610 operates repeatedly, as indicated by a feedback path 615, until operator 499 is satisfied with the imaging and makes the decision, indicated by a decision box 620, to move on to setup the narrowband imaging collection parameters, operation 630. As with visible imaging setup, narrowband imaging setup operates continuously, as indicated by a feedback path 635, until operator 499 decides, at a decision box 640, that he is satisfied with the imaging parameters. At this point operation flows into Operational phase 700.

It will be understood that narrowband imaging setup 630 will typically include generating sample Highlighting Image Representations (HIR), possibly combining these image representations with the visible image stream, and potentially requesting different processing modes be applied to the narrowband image frames to create the HIR.

To initiate Operational phase 700, operator 499 instructs visualization system 10, through user interface 300B and visualization system controller 705, what operational image collection and processing steps are desired. Visualization controller 705 interprets these operator commands and distributes appropriate lower level commands to the other operational elements.

More specifically, in this exemplary flow, the image collection elements, e.g., camera controller 209, illumination modules 110, 120, and image capture hardware 211, begin visible and NIR image collection 710 using the desired NIR: VISIBLE imaging ratio, which ratio primarily affects the timing of activation for the illumination modules 110 and 120 (camera 130 operates identically with either illumination). As each image frame is received, either NIR image capture element 720 or visible image capture element 730 is activated by controller 705, depending, of course, on which illumination module was active when the frame was recorded in the camera.

If the instant frame is the canonical frame 1—a NIR image frame—then NIR image capture element 720 transfers the captured image frame to the HIR generation elements 725. HIR generation elements 725, following the instructions received from controller 705, creates the HIR frame. If the instant frame is one of the N-M visible frames, the frames are transferred to image combiner 740. Combiner 740, also following instructions from controller 705, combines the typically single HIR frame with the generally continuous visible image stream. This combining function is typically an overlay function but visualization system 10 can be configured to generate a variety of HIRs and to combine the HIR and visible image stream in a variety of ways. One of ordinary skill in the art will recognize the many ways in which two images can be combined, ways that are embodied, for example, in photograph processing software applications, e.g., Adobe® Photoshop, available from Adobe Systems Inc., 345 Park Ave., San Jose, Calif. 95110-2704. The combined image(s) are transferred to the display portion of the user interface 300A.

Figure 5A:
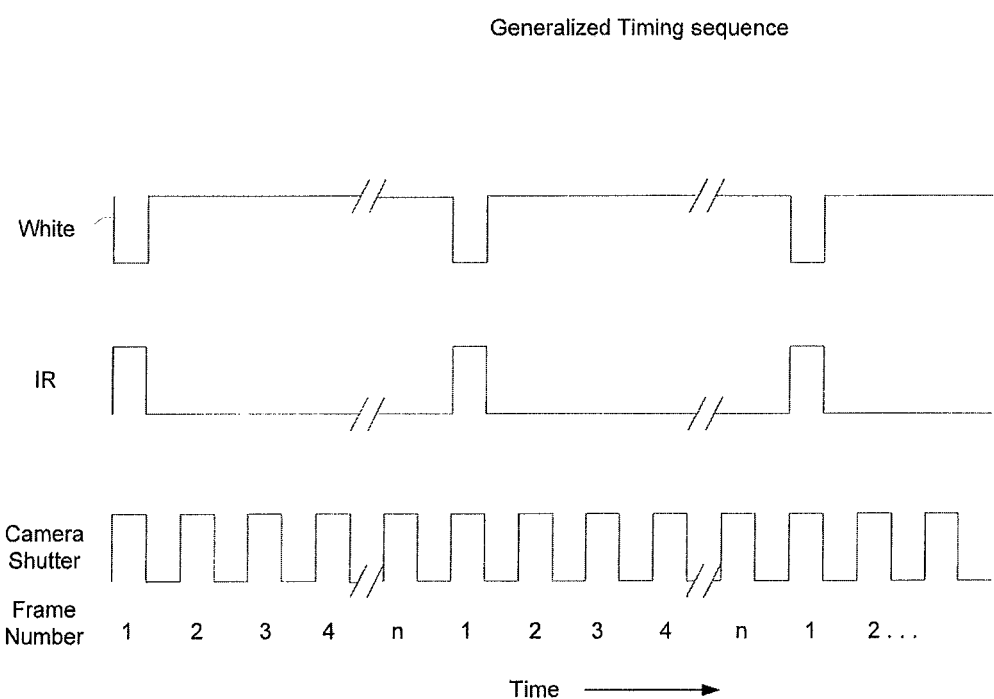
FIGS. 5A and 5B are exemplary timing diagrams relating to illumination and image capture.

FIG. 5A presents a top level timing diagram for an exemplary embodiment of a visualization system 10 that includes one visible light source module 110, one narrowband light source module 120, and one camera 130. The figure displays the activation periods (High=activated, Low=deactivated) as a function of time for the three named elements, with module 110 on the top line, module 120 on the middle line, and camera 130 on the bottom line. The abscissa, time, is scaled in "frame number", starting with the canonical NIR frame 1.

The exemplary timing diagram in FIG. 5A illustrates a 1:N imaging ratio—that is, each NIR frame 1 is followed by N−1 visible frame. Consideration of this timing diagram, in co-ordination with the operational flow described above, will indicate that since every $N^{th}$ recorded frame is an NIR frame, there must be a gap in the otherwise continuous visible image stream. If combiner 740 were to operate rigorously as described above there would be a corresponding gap in the visible displayed image; for one frame time the display would show just the HIR overlay. Of course, in actual operation combiner 740 (or, equivalently, capture element 730) buffers the visible image stream, repeating the most recent visible frame to fill in the one frame gap.

In another exemplary embodiment, visualization system 10 is configured to distinguish between veins and arteries, generally while highlighting both. This differentiation is accomplished by advantageously using at least two narrowband light source submodules 120A and 120B operating at different wavelengths, wherein the veins and the arteries preferentially absorb one of the two wavelengths respectively.

Figure 6:
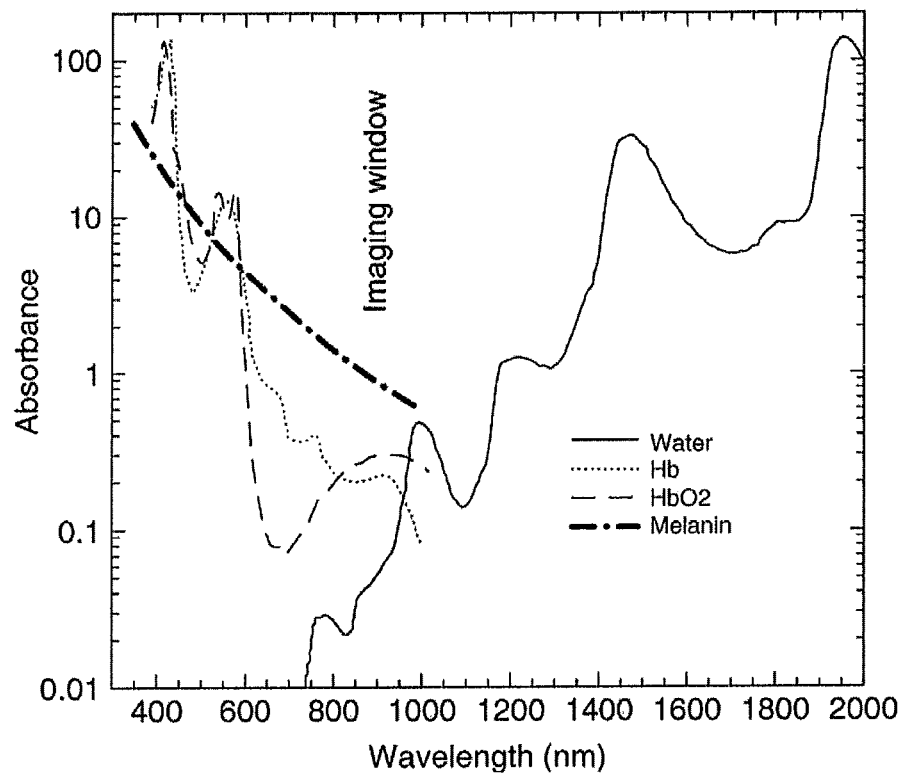
FIG. 6 is a graph of the spectral absorption data for oxyhemoglobin and deoxyhemoglobin.

FIG. 6 displays a graph of the absorption spectra of oxyhemoglobin (HbO2)—found primarily in arteries—and deoxyhemoglobin (Hb)—found primarily in veins—as a function of wavelength ($\lambda$). The "Imaging Window" shown on the graph applies to external tissues. Imaging may be extended below 800 nm for internal tissues because these tissues do not have melanin, whose increasing absorption at visible wavelengths inhibits external tissue vascular imaging. As shown in the figure, the absorption coefficients of both Hb and HbO2 at 800 nm are substantially equal, while the absorption of Hb is about 3 times higher than HbO2 at 700 nm and about ⅓ of the absorption of HbO2 at 1000 nm.

Figure 7A:
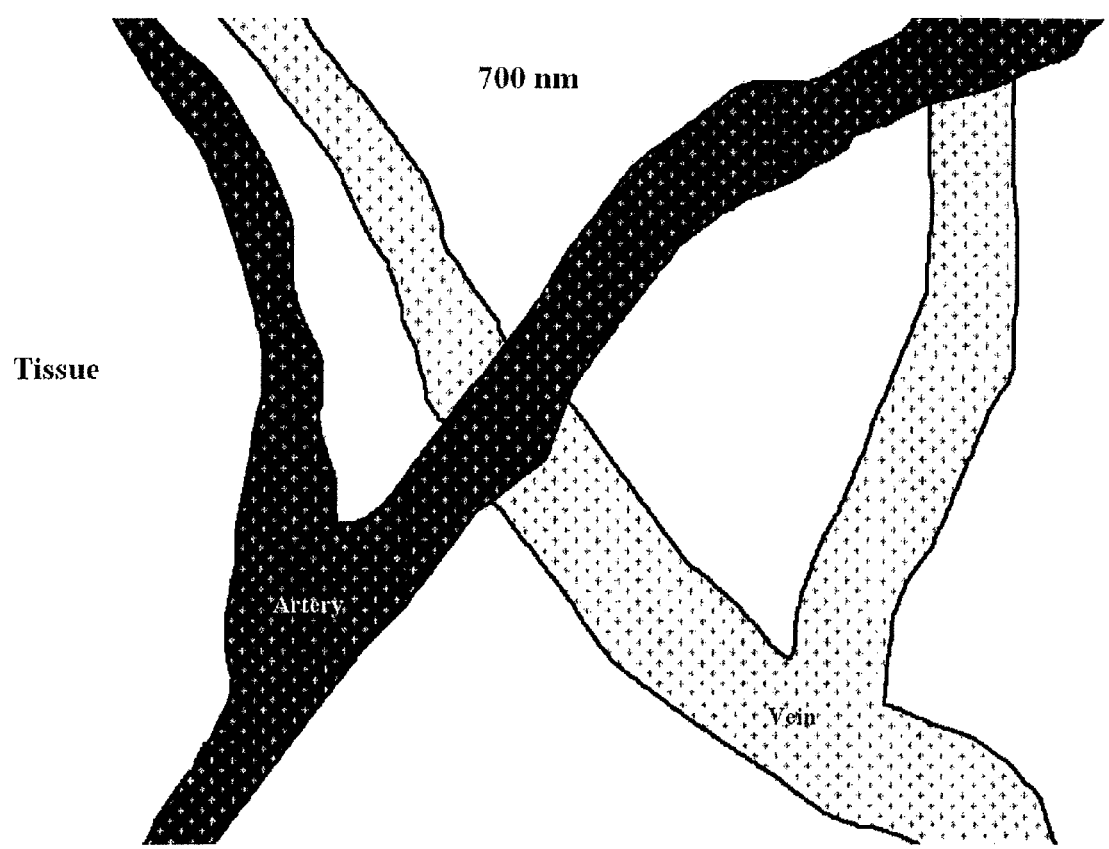
FIGS. 7A through 7C illustrate a hyperspectral technique for differentiating veins and arteries.
Figure 7B:
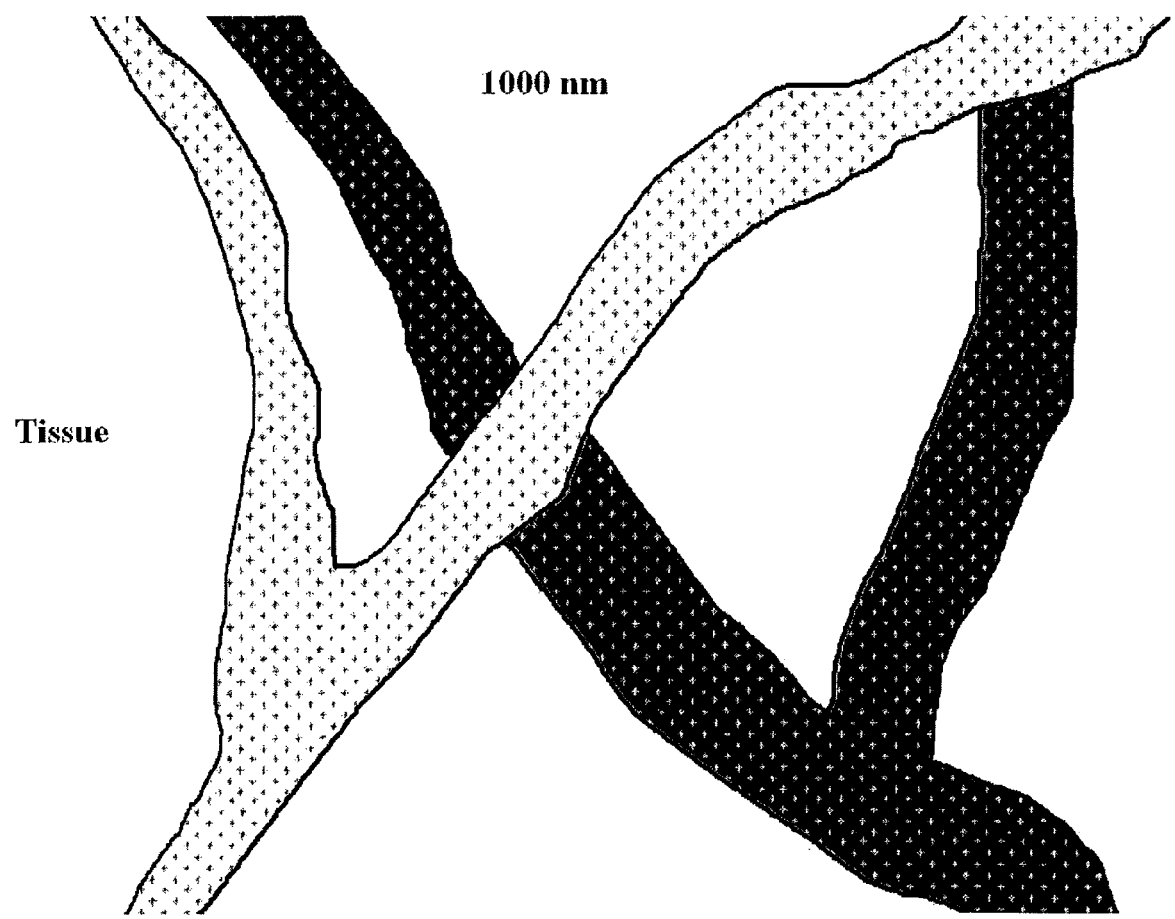

Visualization system 10 can be configured to exploit this phenomenon. Specifically, an embodiment of visualization system 10 that includes two narrowband light source submodules 120A, 120B can be used to independently image the veins and arteries. Consider FIG. 7A, which represents an image captured with 700 nm illumination. Because the absorption of Hb at 700 nm is about 3 times higher than HbO2, veins appear darker than arteries. The converse is true at 1000 nm, as shown in FIG. 7B. To exploit these differences in absorption, visualization system 10, in this embodiment, is configured to operate in a 2:N NIR to visible imaging ratio; that is, sequential NIR frame-pairs at 700 nm and 1000 nm are captured, followed by N–2 visible frames.

Figure 5B:
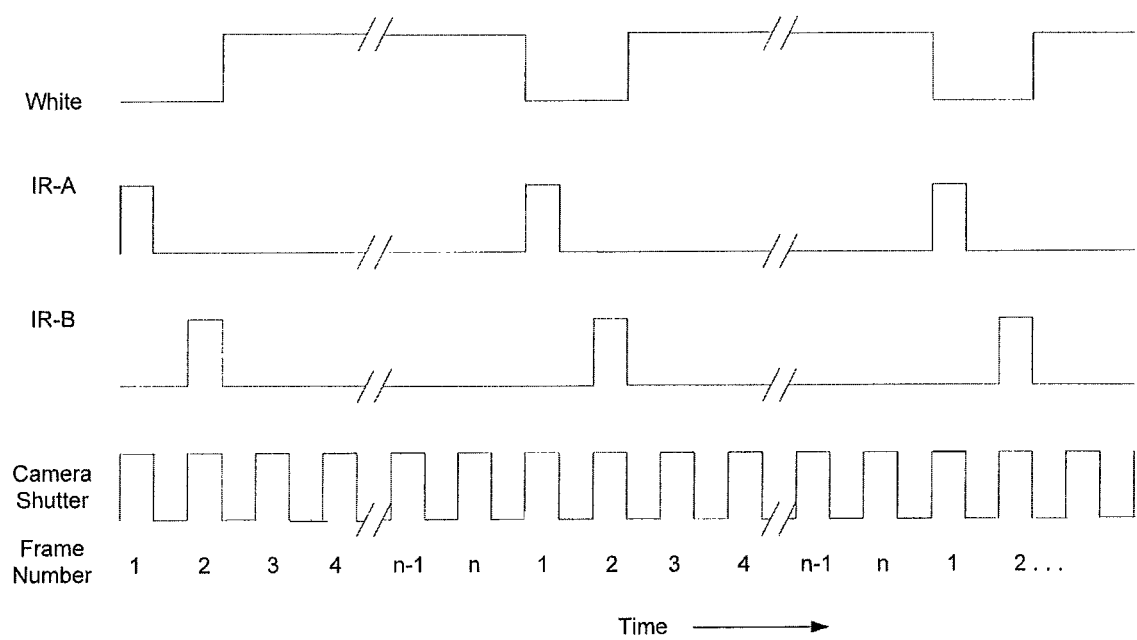

An exemplary timing diagram for a system embodiment configured to exploit this phenomenon, including one visible light source module 110, two narrowband light source submodules 120A, 120B, and a one camera 130 is shown in FIG. 5B. The figure displays the activation periods (High=activated, Low=deactivated) as a function of time for the four named elements, with module 110 on the top line, submodule 120A on the second line, submodule 120B on the third line, and camera 130 on the bottom line. The abscissa, time, is scaled in "frame number", starting with the canonical NIR frame 1 and including the second NIR frame as frame 2. Frame 1 has the 700 nm source turned on and all other sources turned off while frame 2 has the 1000 nm source turned on and all others turned off.

Figure 7G:
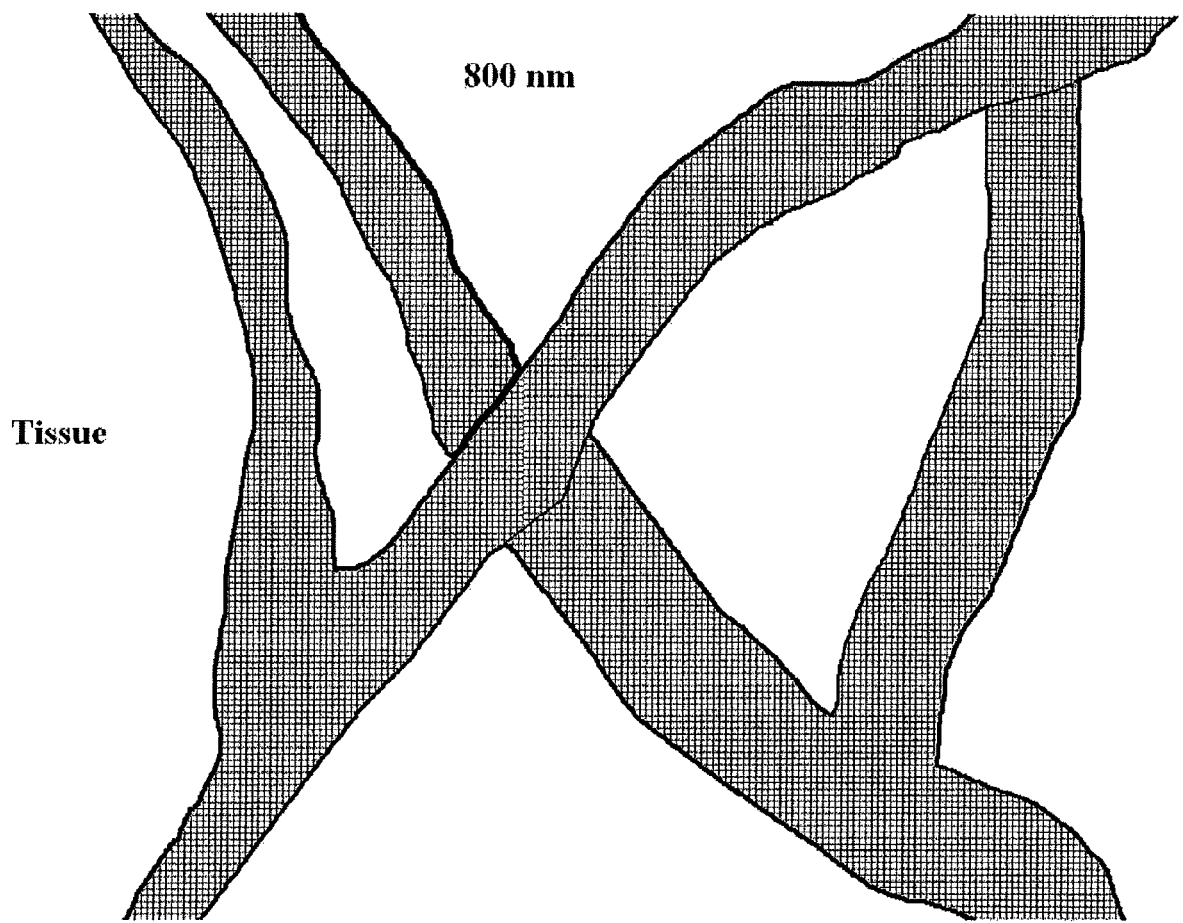

Returning to FIG. 7, in one exemplary processing configuration, the two NIR frames are processed to individually select the veins or the arteries. For example, because the luminance values of arteries in frame 1 are higher than they are in frame 2, if frame 1 is subtracted from frame 2, the calculated luminance values of the arteries is negative and are set to 0. Similarly, the background tissue luminance, being nominally unchanged from frame to frame, also is zero or near zero in the subtracted image. The veins, however, have higher luminance values in frame 2 and thus are the only image elements that retain a significant non-zero value in the subtracted image. Thus, an HIR generated from the subtraction of frame 1 from frame 2 highlights the veins only.

Equivalently, when frame 2 is subtracted from frame 1, the luminance values of the veins and the background becomes substantially 0 and only the arteries remain. If desired, frame 2 minus 1 (HIR of veins) may be added to frame 1 minus 2 (HIR of arteries) to produce an HIR of all vasculature.

Alternatively, in another exemplary processing configuration, the ratios of luminance values (frame 1 divided by frame 2, and frame 2 divided by frame 1) may be used rather than frame subtraction to distinguish veins from arteries.

In yet another exemplary processing configuration, because the absorbances of Hb and HbO2 are about the same at 800 nm, images captured at this wavelength (FIG. 7C) may be used to normalize the images at 700 nm and 1000 nm. Such normalization may be used, for example, to compensate for depth of the vasculature beneath the surface of the tissue. Additionally, background subtraction may also be used to enhance the detection of vasculature in this embodiment.

In other embodiments of visualization system 10, generation of the HIR is enhanced by the use of contrast agents (generally a fluorescent or luminescent compound) injected into the blood stream to increase the absorption of the vasculature relative to surrounding tissues. The increased absorption increased the contrast between the vasculature and surrounding tissues in captured images. In one embodiment, fluorescein (or a similar fluorophore approved for human use) is injected into the blood stream to improve contrast between vasculature and surrounding tissues. Since this fluorophore requires blue excitation light, and since its fluorescence quantum efficiency is quite low, an embodiment to utilize fluorescein includes an illumination module operating at blue/UV wavelengths and a filter that blocks the blue light in the imaging path. The blocking filter requires an extinction ratio in the range of $10^{-4}$ to $10^{-6}$ at the excitation wavelengths. Since Fluorescein emits in the green, a custom matrix filter may be used over image sensor 135, where the green bandpass filters are specifically designed to have an extinction ratio in this range for the fluorescence excitation wavelengths. Alternatively, an embodiment may have two cameras 130, wherein one camera includes the high extinction ratio blocking filter and is dedicated to receiving the fluorescent image.

Visualization system 10, in some embodiments, can be used to detect tumors and establish safe surgical margins during tumor resection. It has been demonstrated in commercially available instruments that differences in elastic scattering properties between normal and abnormal tissues can be used for cancer detection (e.g., the Luma product from SpectraScience, Inc.) while differences in inelastic scattering (e.g. fluorescence) properties between normal and abnormal tissues are also currently being used (e.g., the WavSTAT product from SpectraScience, Inc.). These techniques may be used in some embodiments of visualization system 10 through the capture of frames using one or more blue or ultraviolet (UV) light sources in addition to, or in place of, one or more of the visible or IR sources. In the same way that the HIR of vasculature is overlaid onto color video streams, false-color representations of tumors or abnormal tissue may be overlaid. Such overlays are useful guides for the resection of tumors, as well as for the establishment of safe surgical margins in real time during surgery. These capabilities reduce the probabilities of re-surgeries following conventional pathological analysis of margin biopsy samples, as well as the probability of disease recurrence.

While various embodiments of the innovation have been particularly shown and described, it will be understood by those skilled in the art that various changes in form and details may be made therein without departing from the spirit and scope of the innovation as defined by the appended claims.

I claim:

1. A digital mapping system for mapping a tissue element, comprising:

an access device configured to illuminate and image a tissue region wherein the tissue element may be found, the access device comprising a visible light source, a first infrared light source, and an image sensor; and a visualization system controller disposed in electrical communication with the access device, the visualization system controller comprising an image capture device that is adapted to capture using the image sensor a number of sets of image frames that each include "n" contiguous frames, where the controller is configured to:

control the first infrared light source to illuminate the tissue region, and use the image capture device to capture at least one frame while the first infrared light source is illuminated, and generate a highlighting image representation of the tissue element within a tissue region based upon the captured frames;

and then control the visible light source to illuminate the tissue region, and use the image capture device to capture most or all of the remaining frames of each set of image frames while the visible light source is illuminated, and generate a visible image stream of the tissue region;

combine the highlighting image representation of the tissue element with the visible image stream, to generate a composite tissue image, where the composite tissue image is a video image comprising a visually continuous stream of the visible image with the highlighting image representation of the tissue element combined with the visually continuous stream;

deliver the composite tissue image to an output device;

wherein the tissue element comprises a vascular tissue element;

wherein the visualization system controller is further configured to:

identify the vascular tissue element as being at least one of a venous vascular tissue element and an arterial vascular tissue element;

identify the at least one of the venous vascular tissue element and the arterial vascular tissue element as part of the composite tissue image;

wherein the access device further comprises a second infrared light source, and wherein when identifying the vascular tissue element as being at least one of the venous vascular tissue element and the arterial vascular tissue element the visualization system controller is further configured to:

control the second infrared light source to illuminate the tissue region, where the first infrared light source generates infrared light having a wavelength that is smaller than a wavelength of infrared light generated by the second infrared light source;

subtract the first infrared image from the second infrared image to detect the vascular tissue element as being the venous vascular tissue element;

subtract the second infrared image from the first infrared image to detect the vascular tissue element as being the arterial vascular tissue element; and wherein over the n frames of each set of frames each of the infrared light sources is controlled to illuminate for at least one of the frames, and the visible light source is controlled to illuminate for at least a portion of the remaining n−2 frames, and the visible image stream is buffered so that it is repeated over all of the n frames.

2. The digital mapping system of claim 1, wherein when generating the highlighting image representation of the tissue element within the tissue region based upon the first image of the tissue element, the visualization system controller is configured to:

detect a set of potential boundary pixels of the tissue element relative to the tissue region based upon a magnitude difference in detected image intensity between pixels defining the tissue element in the first image and pixels defining surrounding tissue of the tissue region in the first image; and generate a set of boundary segments of the tissue element from the set of potential boundary pixels to define the highlighting image representation of the tissue element, based on a priori rules.

3. The digital mapping system of claim 1, wherein when identifying the vascular tissue element as being at least one of the venous vascular tissue element and the arterial vascular tissue element the visualization system controller is configured to:

receive vascular tissue element pulse information associated with the vascular tissue element;

compare the vascular tissue element pulse information to a pulse threshold;

when the vascular tissue element pulse information meets the threshold, identify the vascular tissue element as being an arterial vascular tissue element; and when the vascular tissue element pulse information falls below the threshold, the vascular tissue element as being a venous vascular tissue element.

4. The digital mapping system of claim 1, wherein when generating the highlighting image representation of the tissue element within the tissue region based upon the captured frames, the visualization system controller is configured to generate a highlighting image representation of the tissue element within the tissue region based upon an image of the tissue element captured when a fluorescence light source illuminates the tissue region, at least a portion of the tissue region including at least one of a fluorescent compound and a luminescent compound.

5. The digital mapping system of claim 1, wherein:

the tissue element comprises a tumor; and when generating the highlighting image representation of the tissue element within the tissue region based upon captured frames, the visualization system controller is configured to generate the highlighting image representation of the tissue element within the tissue region based upon the first image of the tissue element captured when at least one of a blue light source and an ultraviolet light source of the access device illuminates the tissue region.

* * * * *